United States Patent [19]
Cuffe

[11] Patent Number: 5,596,508
[45] Date of Patent: Jan. 21, 1997

[54] HIGH RESOLUTION MEASUREMENT OF A THICKNESS USING ULTRASOUND

[75] Inventor: John M. Cuffe, County of Centre, United Kingdom

[73] Assignee: Krautkramer-Branson, Inc., Lewistown, Pa.

[21] Appl. No.: 350,956

[22] Filed: Dec. 7, 1994

[51] Int. Cl.⁶ .................................................. G01H 11/00
[52] U.S. Cl. ........................ 364/508; 364/507; 364/563; 364/550; 364/551.01
[58] Field of Search ........................... 73/622, 610, 609, 73/624–627, 618, 597, 598, 600, 615, 644, 592, 602, 611, 621, 635, 637, 638, 640; 364/507, 508, 563, 550, 551.01

[56] References Cited

U.S. PATENT DOCUMENTS

| | | | |
|---|---|---|---|
| 3,554,014 | 1/1971 | Berg et al. | 73/628 |
| 3,848,460 | 11/1974 | Bantz et al. | 73/597 |
| 3,930,404 | 1/1976 | Ryden, Jr. | 73/622 |
| 4,254,660 | 3/1981 | Prause | 73/597 |
| 4,437,332 | 3/1984 | Pittaro | 73/1 DV |
| 4,541,279 | 9/1985 | Schomberg | 73/597 |
| 4,665,751 | 5/1987 | Hüschelrath | 73/597 |
| 4,706,499 | 11/1987 | Anderson | 73/625 |
| 5,063,780 | 11/1991 | Landry et al. | 73/622 |
| 5,287,291 | 2/1994 | Cuffe et al. | 364/507 |
| 5,349,860 | 9/1994 | Nakano et al. | 73/622 |
| 5,351,544 | 10/1994 | Endo et al. | 73/602 |

FOREIGN PATENT DOCUMENTS

| | | |
|---|---|---|
| 0160922 | 11/1985 | European Pat. Off. |
| 4103808 | 8/1991 | Germany. |

OTHER PUBLICATIONS

PCT International Application No. WO92/09864; Int. Publ. Date: 11 Jun. 1992 Applicant: Combustion Engineering, Inc.; Inventor: Zoran R. Kuljis.

Primary Examiner—James P. Trammell
Assistant Examiner—Hal D. Wachsman
Attorney, Agent, or Firm—Polster, Lieder, Woodruff & Lucchesi

[57] ABSTRACT

Apparatus (10) for measuring physical properties of a tube (T). A pulse generator (12) generates an electrical pulse having predetermined characteristics. Transducers (20a, 20b) convert the pulse to an ultrasonic waveform (W) and propagate the waveform at the tube from different directions. Resulting echoes (E1-E3) are converted into electrical response pulses. Another transducer (24a) propagates a similar waveform at a reference object (B) and converts an echo therefrom into a reference electrical response pulse which is combined with each of the other response pulses. Receivers (28a, 28b) receive the combined response pulses and convert them to digital data stored in a memory (32). A processor (36) reconstructs each combined waveform and determines from each reconstruction a value representing a physical characteristic of the tube. This involves performing a "real time" evaluation of the combined waveform to determine if it meets threshold criteria. If it does, a linear interpolation and finite impulse response on the digital data is performed to precisely measure time of flight (TOF). A processor (54) mathematically combines respective TOF values derived from a reconstruction to ascertain other physical characteristics of the tube. Each characteristic value is compared with a predetermined set of limits to determine if a measured value fall within the limits. Results of the comparison are displayed to an operator, and a permanent record of the values is made.

37 Claims, 5 Drawing Sheets

HIGH RESOLUTION MEASUREMENT OF A THICKNESS USING ULTRASOUND

BACKGROUND OF THE INVENTION

This invention relates to non-destructive testing, and more particularly to the use of ultrasonics to perform extremely high resolution testing of the properties of a material.

Non-destructive testing of material properties is well-known in the art. One method of non-destructive testing is the use of ultrasonic waves. This method is used, for example, to test the material's thickness, and detect flaws in the material. The method of ultrasonic testing involves generation of an ultrasonic waveform, propagating the waveform into the material, detecting a return, reflected waveform or echo, and processing the echo waveform to determine parametric values.

Previous methods of ultrasonic testing have involved the measurement of a particular characteristic of the ultrasonic waveform. These include detecting a zero-crossing of the waveform, or detecting when the amplitude of the waveform exceeds some predetermined threshold, or detecting when the waveform amplitude reaches a peak or maximum value. Various methods have been used to perform measurements using ultrasonic waves. One such method involves use of a stable, free running oscillator having a known and accurate frequency. Pulses from the oscillator are counted by a counter which is started and stopped in response to a sensed characteristic of the ultrasonic waveform. The resultant count, for example, represents the ultrasonic signal's time of flight (TOF); i.e., the transit time for the waveform to be propagated into the test object and the return echo detected. This "single shot" testing method is satisfactory, but it does have some drawbacks. It is limited in resolution to measurements of approximately 0.001 inches, or a time of flight of approximately 8 nanoseconds ($8*10^{-9}$ sec.). Because it involves a single sample, there are limits as to the accuracy of the measurement. Accuracy can be improved by a factor of ten by taking multiple samples and developing an arithmetic average value for the samples taken. But, this may require more time than is available for the measurement.

One approach utilizes a series of analog measurements. Here, an integrator accumulates a voltage over a given time window. The integrated voltage value is then measured using a digital voltmeter. The result is an accurate measurement, but one which is effected by the amount of drift in the analog circuits. Other alternate approaches employ other combinations of digital and analog circuits and techniques. In general, use of analog techniques provides some interpolation of direct digital techniques to improve the accuracy of the measurements.

Further with respect to current processing techniques, it is common to measure time of flight to a fixed threshold level of the waveform; for example, 50% of the full output of a screen on which the waveform is monitored. Problems arise because normal variations in the amplitude of the waveform will move this 50% point due to changes in the slope of the waveform. This, in turn, effects the time of flight calculation. Where time of flight is based upon reference to a zero crossing of the waveform, slight variations in the waveform caused by its lower frequency components will also effect the accuracy of the time of flight calculations.

Despite the measurement accuracy which is achievable with existing techniques, there is a practical limit beyond which improvements are not easily achieved. This presents a major concern where very small measurements are required and where a high degree of accuracy is needed. In nuclear reactors for example, a zirconium alloy tubing is used. Not only is the material expensive, but the tubing is a very small tubing, having a wall thickness which must be measured to an accuracy on the order of 10 microinches ($10*10^{-6}$ in.). Because of the amount of zirconium tubing used in a reactor facility, it represents a substantial cost. Also, because of the nature of the facility, it must be precisely measured to insure its suitability for installation. If the diameter of the tubing cannot be precisely measured, if its inner and outer diameters and eccentricity cannot be accurately determined, otherwise acceptable tubing may be unnecessarily rejected. A precise measurement technique and method which will enable the physical characteristics of the tubing to be precisely determined, during volume production of the tubing, might lower the reject rate of the tubing. This, in turn, would not only insure that suitable tubing were accepted for use in the facility, but also that the overall manufacturing costs of the tubing are lowered.

Finally, with respect to the noted problems caused by threshold and zero crossing variations, there is need for a technique by which any variations are readily accounted for without impacting the speed with which accurate data is obtained.

SUMMARY OF THE INVENTION

Among the several objects of the present invention are apparatus and a method for non-destructive testing of an object; the provision of such a apparatus and method for using ultrasonic techniques to precisely measure the physical characteristics of a tubing or the like used in critical installations where safety is of paramount importance; the provision of such method and apparatus for testing substantial lengths of tubing on a production basis and to provide quick and accurate readings o f the physical properties of the tubing being tested; the provision of such a method and apparatus to provide measurement accuracies on the order of 10 microinches using ultrasonic pulses whose times of flight are measured to an accuracy of 100 picoseconds ($100*10^{-12}$ sec.); the provision of such method and apparatus to perform ultrasonic testing at a rate of at least 10 khz; the provision of such a method and apparatus to generate and transmit an ultrasonic waveform, to receive and store a return reflected waveform for each transmitted waveform, and to subsequently process the stored waveform information to determine the physical characteristics being measured, and whether the measured values fall within predetermined test limits; the provision of such method and apparatus to mathematically reconstruct the flight time of each waveform and its echo and to determine the pertinent measurement information from the reconstruction; the provision of such a method and apparatus utilizing linear interpolation and finite impulse response (FIR) techniques to precisely determine zero crossings of the response waveform and using this information establish precise time of flight values which relate to the physical characteristics being measured; the provision of such a method and apparatus to be calibrated prior to the beginning of each test cycle, to independently monitor the testing environment during testing, and to compensate the data for sensed environmental changes so to maintain the accuracy of the test results; the provision of such a method and apparatus to provide an indication if an out of tolerance condition is sensed; the provision of such a method and apparatus to provide a printout of all the measured parameters so there is a permanent record of the measured properties for each tube tested; the provision of such a method and apparatus by which, for each separate processed waveform and its accompanying echo, the true peak value and zero crossing points are readily ascertained so accurate threshold comparisons zero crossing references are available to use in determining the values measured by the particular test; and, the provision of such a method and apparatus which is easy to use.

In accordance with the invention, generally stated, apparatus is provided for measuring the physical properties of an object such as a tube using an ultrasonic testing technique. An ultrasonic waveform having a predetermined set of waveform characteristics is first generated. The waveform is simultaneously propagated at the tubing from at least two different directions and respective return reflected response waveforms from the tubing are detected. The waveform is separately propagated at a reference object and a return reference waveform is detected. The reference return waveform is combined with each of the other two response waveforms. The two resulting combined waveforms are separately stored. A multi-channel processor simultaneously, separately reconstructs each combined response waveform and determines from each separate reconstruction a value representing a physical characteristic of the tube. This is done using linear interpolation and FIR techniques to precisely establish zero crossing points of the response waveform to establish time of flight values related to the tube characteristics being measured. The resulting values are supplied to a separate processor having a section for mathematically combining the respective values derived from the reconstructions to ascertain yet another physical characteristic of the tube as a function of the processed waveform values. Another section of the processor compares each of the physical characteristic values with a predetermined set of limits for each of the values to determine if the measured values fall within the limits.

As a method, the present invention includes the steps of generating an ultrasonic waveform having a predetermined set of waveform characteristics, simultaneously propagating the waveform at the tube from at least two different directions, and detecting respective reflected response waveforms or echoes from the tube, each response waveform representing echoes of the respective propagated waveform. The waveform is further propagated at a reference object and the resulting echo detected as a reference response waveform. The reference response waveform is separately combined with each of the other response waveforms. The method further includes the steps of separately storing each combined response waveform, simultaneously, separately reconstructing each combined waveform and determining from each separate reconstruction a value representing a physical characteristic of the tube; and mathematically combining the respective values derived from the separate reconstructions to ascertain other physical characteristics of the tube as a function of the other values. This is done, in part, using linear interpolation and FIR techniques to precisely establish zero crossing points of the response waveform to establish time of flight values related to the tube characteristics being measured. Finally, the method includes the step of comparing each of the physical characteristic values with a predetermined set of limits for each of the values to determine if the measured values fall within the limits. Other objects and features will be in part apparent and in part pointed out hereinafter.

BRIEF DESCRIPTION OF THE DRAWINGS

Corresponding reference characters indicate corresponding parts throughout the drawings.

DESCRIPTION OF A PREFERRED EMBODIMENT

Referring to the drawings, an apparatus 10 of the present invention is for use in the non-destructive testing of an object to measure certain physical characteristics of the object. While the apparatus and method of the invention are described with respect to the measuring of the physical characteristics of a hollow tube T, it will be understood that the apparatus and method are also useful in other testing applications where very small values are required to be very precisely measured; particularly in a production or manufacturing setting. In FIG. 1B, for example, tube T is shown to have an outside diameter o.d., a sidewall S of thickness t, and an inner diameter i.d. For certain applications, it may be necessary or desirable to measure the o.d of the tube to an accuracy of $100*10^{-6}$ inches, and the wall thickness to an accuracy of $10*10^{-6}$ inches. It is known that wall thickness can be determined as a function of the time of flight of an ultrasonic wave propagated to and through the tube's sidewall. However, the time of flight of such a wave is on the order of $100*10^{-2}$ seconds. In such a circumstance, conventional measurement techniques do not provide the desired level of accuracy required to pass or fail the tube. The apparatus and method of the present invention do provide this accuracy.

Tube T is tested while being drawn through a chamber 12 which is filled with a liquid medium L such as water. One end Te of the tube is connected to an appropriate drive mechanism 14 by which the tube is pulled through the chamber at a desired rate of travel. As it is being drawn through the chamber, the tube is also rotated. By drawing the tube through the medium in a controlled manner, sufficient information can be developed about the tube that not only information such as i.d., o.d., and wall thickness can be obtained, but also information relating to the circularity or ovality or eccentricity of the tube about its longitudinal axis.

Figure 1A:
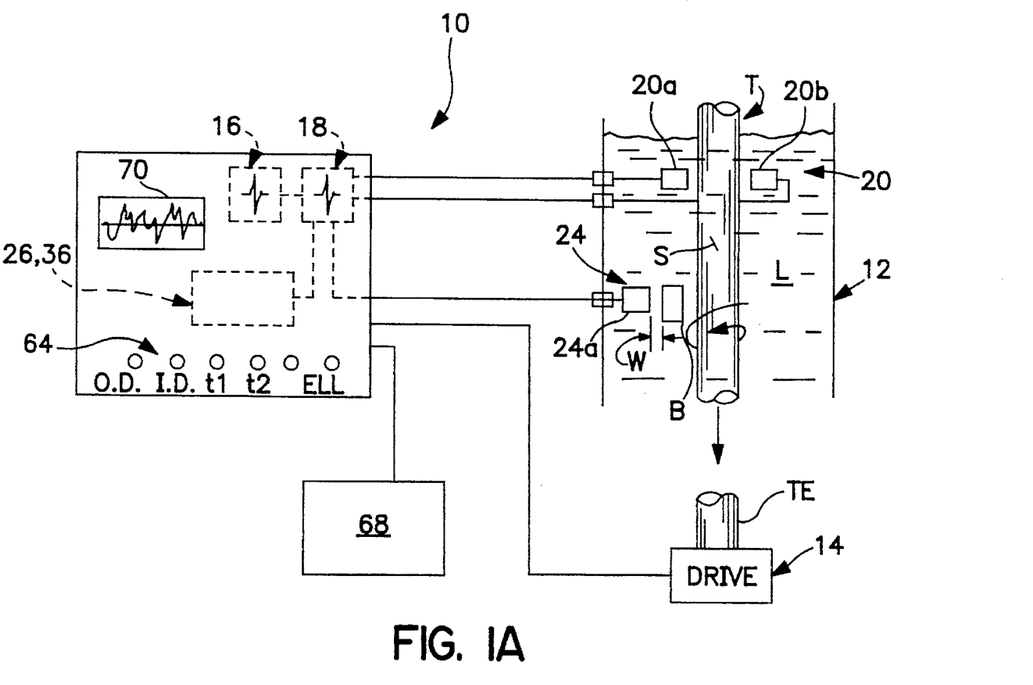
FIGS. 1A and 1B are simplified representation of a test facility for the present invention to test the physical characteristics of a tube.
Figure 1B:
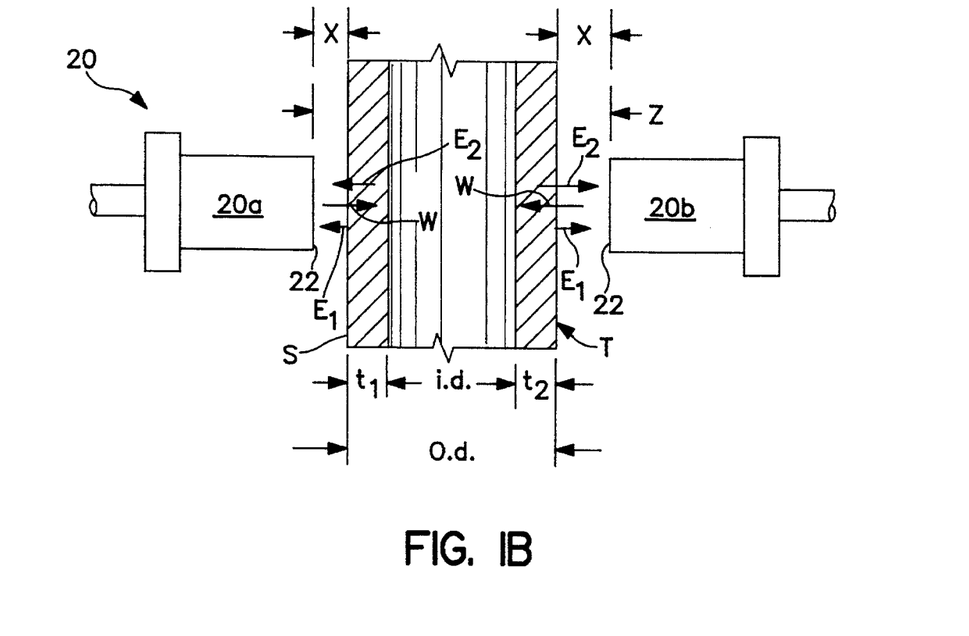

Referring to FIG. 1A, apparatus 10 includes a means 16 for periodically generating an electrical pulse having a predetermined set of pulse characteristics. Pulse generating means operates at a frequency of, for example, 10 KHz. The output of the pulse generating means is supplied to an amplifier means 18. Each electrical pulse generated by means 16 is supplied to a transducer means 20 which converts the pulse to an ultrasonic waveform. As shown in FIGS. 1A and 1B, transducer means 20 includes first and second ultrasonic transducers 20a and 20b respectively. This transducers are located in chamber 12, submerged in the liquid medium. The transducers are spaced apart from each other and are also spaced from an outer sidewall surface of the tube a known distance. Preferably the transducers are positioned on opposite sides of tube 180° apart from each other. Prior to the beginning of a test, a calibration procedure is executed during which an exact distance z (see FIG. 1B) between the opposed faces 22 of the transducers are determined. Calibration is performed in accordance with the teachings in coassigned U.S. Pat. No. 3,554,014 and 3,848,460 which are incorporated herein by reference. The distance information derived as part of the calibration is entered in a memory portion of the apparatus for use as described hereinafter. In addition, a distance x is determined which is the distance between each transducer face 22 and the outer surface of tube sidewall S. Again this information is retained for use in subsequent processing.

Ultrasonic transducers 20a, 20b simultaneously propagate an ultrasonic waveform W at tube T from the opposite sides of the tube. As is well-known, when an ultrasonic wave impinges on an outer surface of an object, a return reflected waveform or interface echo E1 is produced. As the waveform W then propagates through sidewall S of tube T subsequent echoes are produced whenever a discontinuity is encountered. Tube T is, as noted a hollow tube, and only air fills the tube. Additional echoes E2, E3 referred to as backwall echoes are subsequently produces as the waveform propagates through the tube sidwall through to the inner surface of the sidewall. At the respective transducers 20a, 20b, the echoes E1–E3 are converted from ultrasonic waves into electrical response waveforms. The response waveforms are supplied as outputs of the transducers for processing.

Figure 3:
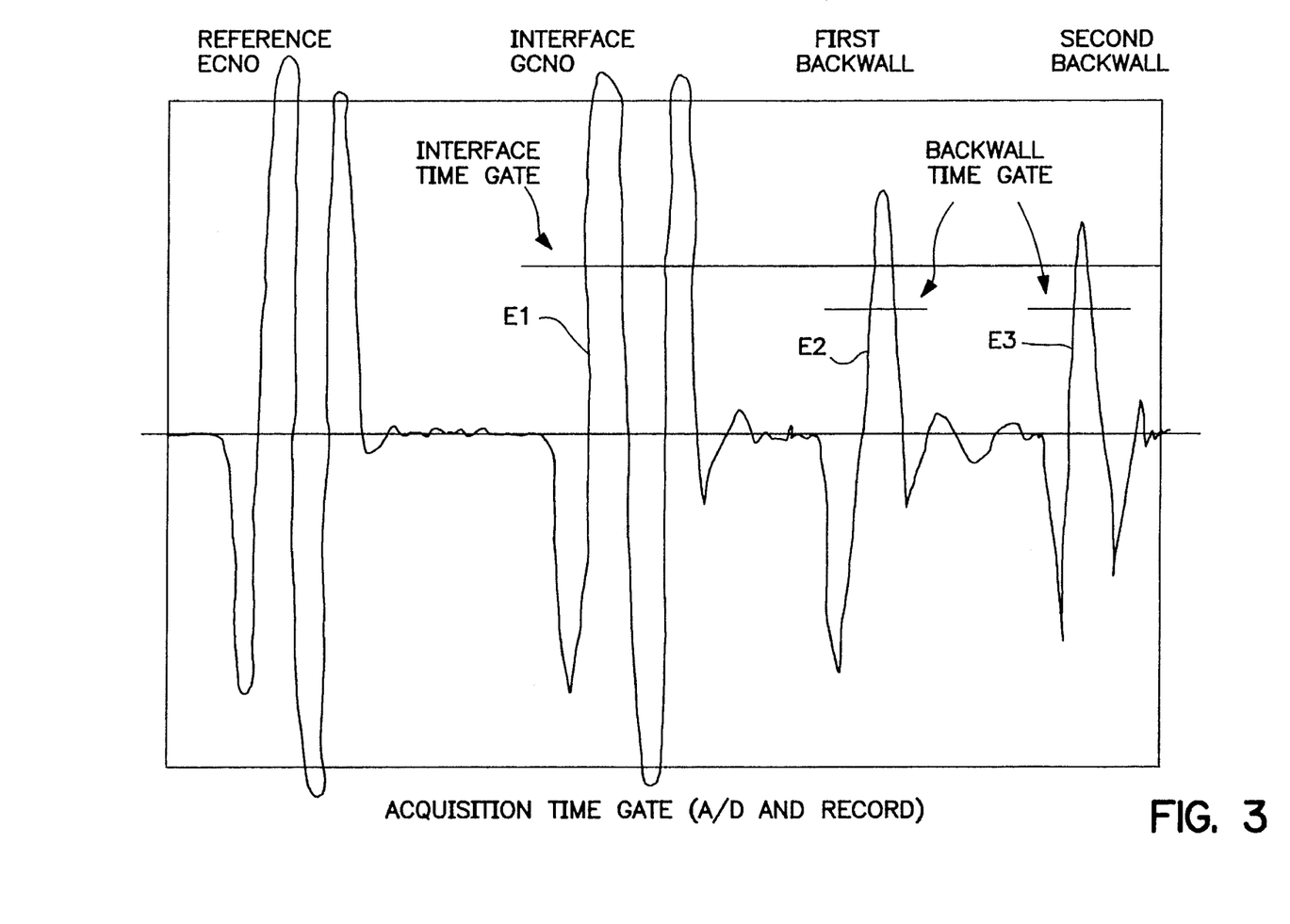
FIG. 3; is a representation of a combined reflected response waveform or echo as processed by the apparatus.

It is an important feature of the invention to compensate the test results for environmental changes which take place during testing. The signal characteristics of ultrasonic waveforms are effected, for example, by temperature changes in the liquid medium in which transducers 20a, 20b are submerged. That is, as the liquid temperature changes, the velocity at which ultrasonic waves travel through the liquid may change substantially. Unless appropriate compensation is made during signal processing by the apparatus, inaccuracies can occur. Compensation means 24 of the apparatus includes an ultrasonic transducer 24a which is located within chamber 12 and is also submerged in the liquid medium. Transducer 24a located a fixed distance w from a fixed reference object B. The distance w is less than the distance x. The electrical pulses supplied to transducers 20a, 20b, are also supplied to transducer 24a. The return echo from the ultrasonic waveform propagated by transducer 24a at object B is converted to an electrical return pulse and supplied to back to the apparatus together with the return pulses from the two test transducers. The signal from transducer 24a is then incorporated into the return signals from both of the other transducers. This is as shown in FIG. 3. As shown therein, a combined return response for each transducer 20a, 20b has, as a first component, the return reference response from transducer 24a. It appears first because, as noted, transducer 24a is placed nearer reference object B than either of the transducers 20a, 20b is placed to tube T. Next, is the portion of the electrical pulse representing interface echo E1. This is followed by the portion of the electrical pulse representing echoes E2, E3. The remainder of the pulse are re-reflections of the ultrasonic waveform. This portion disappears as the waveform energy dissipates.

Figure 2:
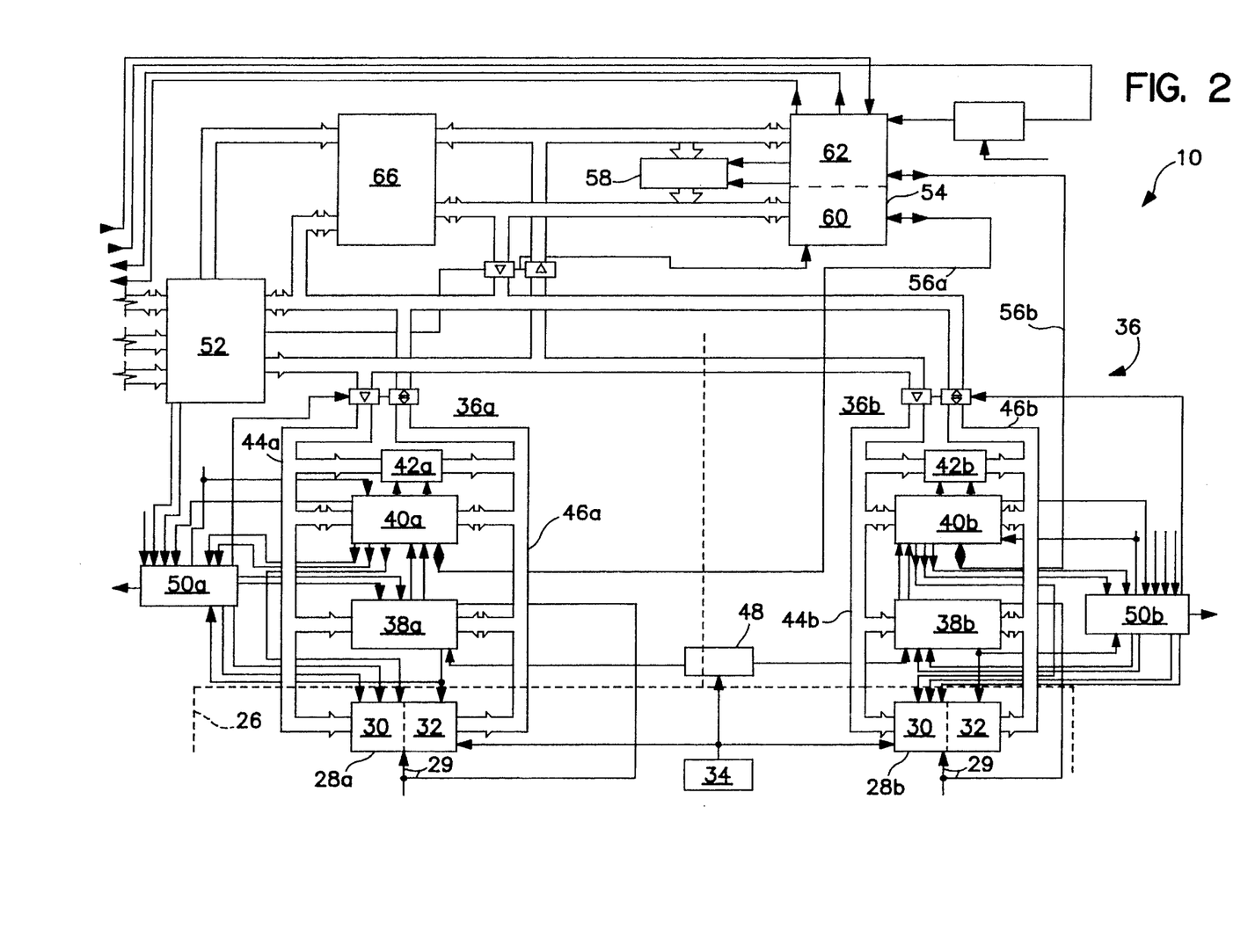
FIG. 2 is a block diagram of a signal processing portion of the apparatus.

Referring to FIG. 2, apparatus 10 next includes receiving means 26. Means 26 includes a first digitizer 28a and a second digitizer 28b. One of the combined return pulses is supplied as input to one of the digitizers; and the other combined return pulse is supplied as an input to the other digitizer. The waveforms are supplied over respective input lines 29a, 29b. Each digitizer performs two functions. First, each digitizer has an analog-to-digital converter section 30 for converting the analog signal input to the digitizer to a converted digital signal. Second, the digitizer has a memory section 32 in which each of the converted signals are stored at unique addresses within the memory. Memory section 32 is, for example, a random access memory (RAM). A 200 Mhz. oscillator 34 provides clock signals to each digitizer. For a 10 khz signal, clocking at the 200 Mhz rate provides a resolution of 5 nanoseconds ($5*10^{-9}$ sec.). Thus, the data stored in adjacent memory addresses represents points on the response waveform curve which are 5 nanoseconds apart.

Apparatus 10 further includes a processing means indicated generally 36 for simultaneously, separately reconstructing each converted waveform. The processing means has parallel channels 36a, 36b. The converted waveform from one transducer 20a or 20b is processed in one channel, and the converted waveform from the other transducer is simultaneously converted in the other channel. Each channel includes a gate 38a, 38b respectively, digital signal processors 40a, 40b respectively, an EPROM 42a, 42b, an address bus 44a, 44b respectively, and a data bus 46a, 46b respectively. The 200 mhz. output signal of oscillator 34 is supplied to a divider 48 which produces a 100 mhz. output to each of the gates 38a, 38b. Signal flow over the respective control and data buses is monitored by respective arbitration units 50a, 50b; one unit being associated with each respective processing channel. The respective EPROMs are programmed to control data flow between the digitizers, the gate, and the digital signal processors over the respective data buses using commands transmitted to each of these elements over the respective control buses. Processing means 36 interfaces with a quiet bus at a quiet bus interface 52. Inputs to the processing means, and outputs from the processing means are routed over a quiet bus via this interface. The operation of a quiet bus is described in coassigned U.S. Pat. No. 5,287,291 which is incorporated herein by reference. Accordingly, operation of a quiet bus will not be described.

Figure 4:
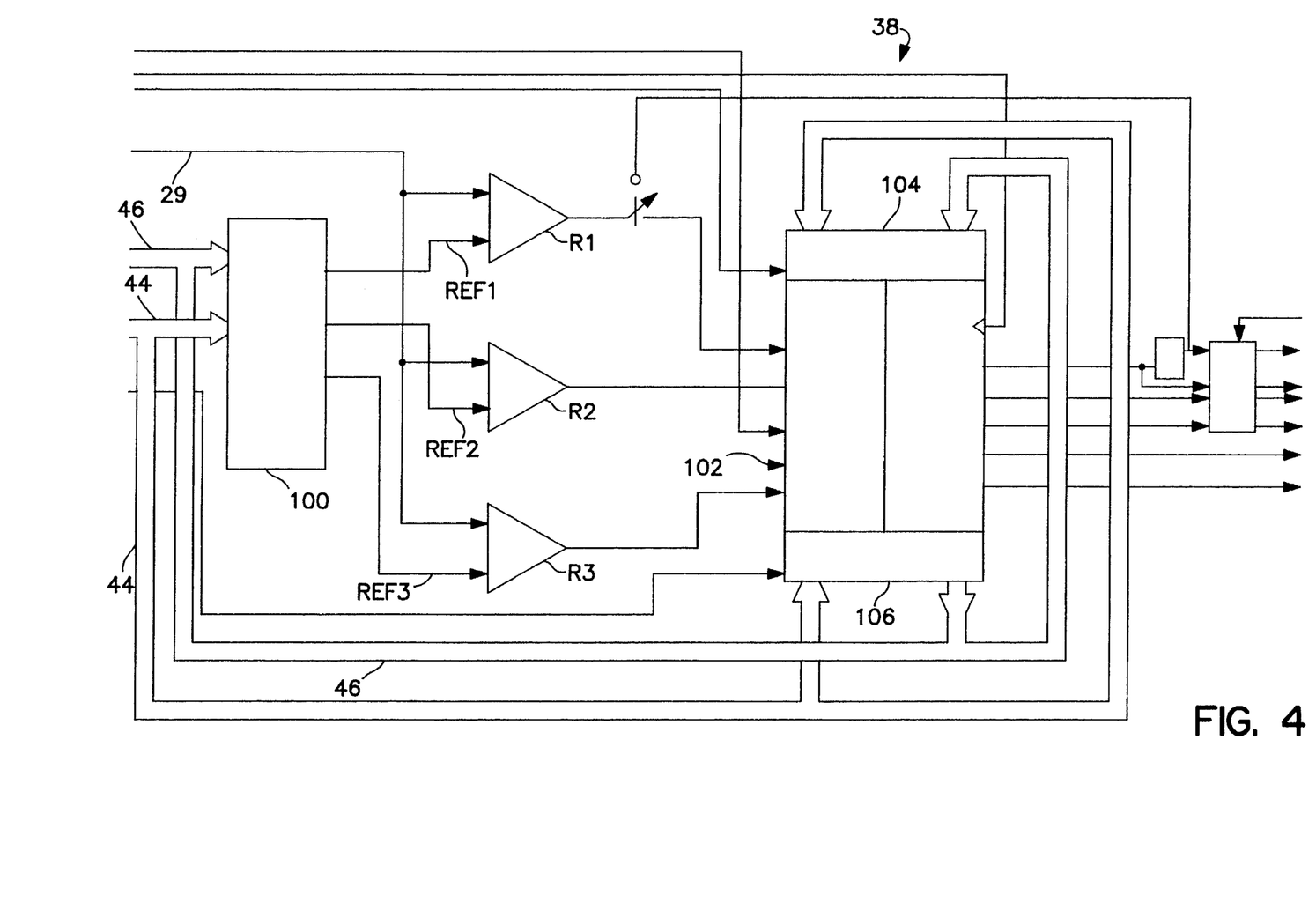
FIG. 4 is a representation of a gate portion of a waveform signal processor for performing an initial waveform evaluation.

In operation, as each combined waveform is supplied as an analog input to a digitizer 28 over an input line 29, it is simultaneously supplied as an input to the gate 38 of that processing channel. The gate acts as a filter to determine if the data represented by the converted waveform is valid data. It does this by making an initial TOF comparison of the input waveform with a preset threshold value. As shown in FIG. 4, the response waveform input on line 29 is supplied as one input to each of three separate comparators R1–R3. Three comparators are used because the separate reflections or echoes E1–E3 are used for this initial determination. A reference threshold unit 100 has separate threshold values which are used as a second input to each of the comparators. Each threshold value is a fixed value continuously supplied as an input to a particular comparator. Thus, a reference input REF1 is supplied to comparator R1 at a time when echo E1 should have a zero crossing, a reference REF2 is supplied comparator R2 at the time when echo E2 should have a zero crossing, and reference REF3 is supplied comparator R3 at the time when echo E3 should have a zero crossing.

An appropriate output is supplied from each comparator to a control logic 102 of the gate. Operation of the control logic is such that it is enabled to receive an input from the respective comparators only at a time when a threshold value should appear in the response waveform. Otherwise, the control logic does not receive or act upon outputs from the comparators. Control logic 102 has both a gate setup register 104, and a gate TOF register 106. Data and address information from buses 44 and 46 are supplied to these respective registers. As storing of the digitized response waveform data occurs, digitizer 28 provides gate 38 both the data values and memory address locations for each of the respective zero crossings. Logic unit 102 then supplies the respective first, second, and third memory address locations to the data acquisition digital signal processor 40 together with a validity or accept signal. This instructs the processor that the converted response waveform should be further processed by the processor 40.

The digital signal processors now reconstruct each converted waveform and determine from each separate reconstruction values representing the thickness of the tube sidewall on the opposite sides of the tube. These are the values t1, t2 shown in FIG. 1B. To achieve the desired accuracy, the digital signal processors employ both a linear interpolation technique and a finite impulse response technique to reconstruct the response waveform particularly in the region of a zero crossing of the respective reflections. The initial "real time" processing within gate 38 provides the signal processor with starting locations for this reconstruction. Because the same process is employed with respect to each zero crossing reconstruction, only one reconstruction is described in detail.

Figure 5A:
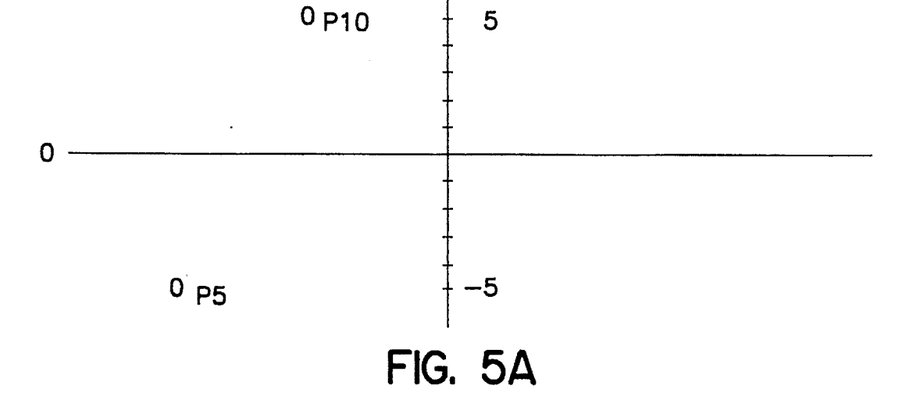
FIG. 5A represents adjacent data points on the response waveform.

Referring to FIG. 5A, assume that the initial processing within gate 38 indicates that a zero crossing occurs at a memory location P10. The previous data point is indicated P5; and as noted, the spacing between the data represented by these points is 5 nanoseconds. Because of the accuracy requirements of the test being performed, the actual zero crossing point must be known to an accuracy of 1 nanosecond. Accordingly, when processor 40 begins its waveform reconstruction, it first evaluates the data point P10 to determine if it is the zero crossing point. For the example shown, data point P10 has a value of +5. Since this does not reflect a zero crossing point, processor 40 then accesses the memory address P5 for the previous data point and determines its value. In the example, this is a value −5. The processor now knows the zero crossing point has occurred somewhere within the 5 nanosecond interval between P5 and P10. Had point P5 also had a positive value, processor 40 would have moved to the previous data point. Or, if point P10 had had a negative value, the processor would have moved to the subsequent data point.

Figure 5B:
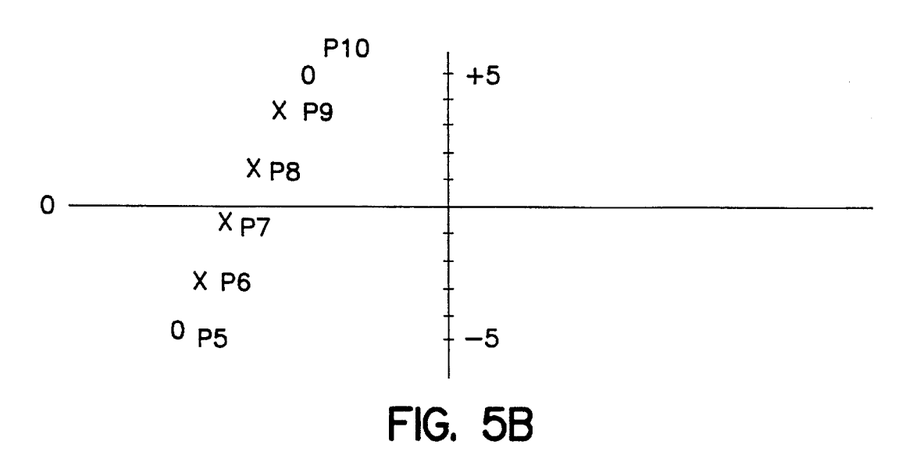
FIG. 5B illustrates a linear interpolation performed on the data points of FIG. 5A; and, FIG. 5C illustrates a best curve fit performed by a finite impulse response technique on the data of FIG. 5B.

Having established that the zero crossing occurs within the 5 nanosecond interval between P5 and P10, processor 40 next performs a linear interpolation between the two points to construct a waveform approximate shape between these points. The results of the linear approximation are shown in FIG. 5B. As shown in FIG. 5B, four new data points P6–P9 are created, as are their respective values of −3, −1, +1, and +3. And, based upon this interpolative process, the zero crossing is found to have occurred between points P7 and P8. Since these created points are spaced 1 nanosecond apart, the zero crossing point is now more accurately established.

Figure 5C:
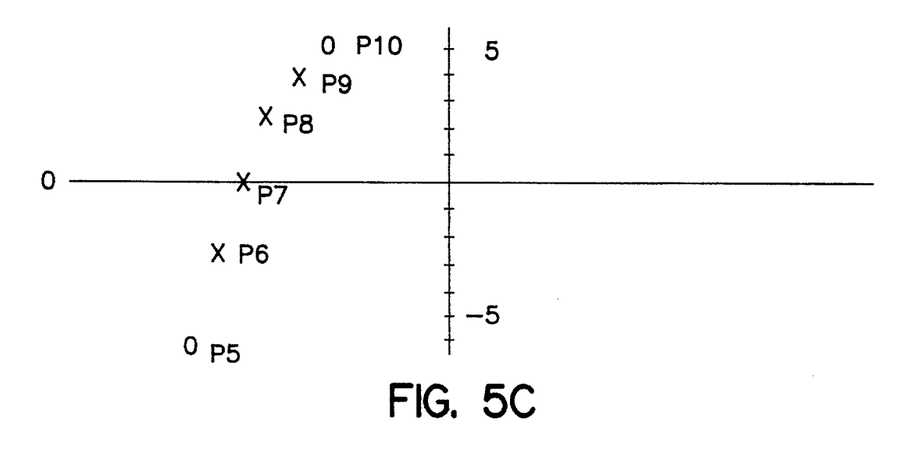

For measurement of the tube diameters, the results from the linear interpolation provide sufficient accuracy to meet the test requirements. The measurement of tube wall thickness t is actually a difference measurement based upon the respective TOF's for two different echoes. To measure the wall thickness to the desired accuracy of $10*10^{-6}$ inches, it is necessary to measure the zero crossing even more precisely than as shown in FIG. 5B. Further, while the linear interpolation provides a more accurate location of the zero crossing than that established by the initial gate 38 evaluation, it will understood that the response waveform is actually a curved waveform, not a straight line. If viewed on an oscillograph or strip recording on an appropriate scale, it would be seen that the response waveform is indeed a curved waveform. For the wall thickness measurement, the zero crossing is measured to an accuracy of $30*10^{-12}$ seconds. To obtain this level of accuracy, the upsampled response waveform of FIG. 5B is recalculated using a finite impulse response filter. This is digital filtration process that produces an "upsampled", higher resolution waveform as shown in FIG. 5C. Using the FIR technique, the two data points P5 and P10 are recalculated (to correct the data values for random noise, for example). The technique further performs a best fit between the data points to adjust the data values to a curve extending between the adjusted original data points. As part of this process, the sample data is upsampled by a factor of five to create the additional data points. In FIG. 5C, for example, the result of the FIR process is to adjust the data value of point P5 from −5 to −6 and fit the points P6–P9 to a curve extending between points P5 and P10. As a result, the zero crossing of the return waveform is shown to have shifted to occur at point P7.

With respect to the reference portion of the response waveform, processor 40 averages the TOF represented by this portion of the response waveform over a large number of responses. For example, the average is taken over the last 500–1000 responses. This can be done because reference object B is fixed and the distance between the object and transducer 24a is invariable. Accordingly, the only change in the TOF of the response is due to temperature changes in the liquid medium which effect the waveform velocity through the medium. By tracking any change in the TOF, the liquid's temperature can also be tracked.

It is important to note that the waveform processing which has been done has not been done in "real time", but rather on a store and retrieve basis. For, while an initial evaluation of the combined waveform was done as the waveform information was received by the processing means, the actual TOF values were determined based upon a reconstruction of the waveform. In addition, this reconstruction, and the remainder of the waveform processing which is subsequently described, all occurs within the 10 khz cycle time of the apparatus. Accordingly, no data is lost, and the test results are readily available to the operator.

Processing means 36 next includes a third and separate digital signal processor 54 to which the results obtained from processors 40a, 40b are supplied. Each processor 40a, 40b supplies its results to processor 54 over respective serial data buses 56a, 56b. Whereas processors 40a, 40b evaluated the response waveforms on a time basis; i.e., determining the TOF values for various portions of the response waveform, processor 54 uses these results to develop values representing physical characteristics of the tube. Operation of processor 54 is controlled by a program stored in an EPROM 58. Processor 54 first includes computing means 60 for mathematically combining the TOF values corresponding to the respective tube thickness values to determine the i.d. of tube T. As noted, during an initial calibration of the apparatus, a distance z between the transducers is established, as is a distance x between each transducer and the outer surface of the tube. The computing means now determines the actual distance between a transducer and the outer surface of tube sidewall S from the appropriate time of flight value. Further, the values representing the tube sidewall thicknesses t1, t2 on opposite sides of the tube are determined by the computing. In each instance, the computing means converts the time value to a distance value as a function of the known propagation times of the waveforms through the liquid medium and the material from which the tube is made. The TOF value for the reference waveform enables adjustments to be made based on any temperature changes in the liquid medium. By subtracting the respective values x from the established distance value z, processor 54 computes the o.d. of tube T. Next, by subtracting the values t1, t2 from the o.d. value, the i.d. of tube T is computed.

Processor 60 also includes means 62 for comparing the respective tube sidewall thickness and computed tube outer and inner diameter values with a predetermined set of limits. These limits are established for each of the values. Based on the comparisons, an indication can be provided to the test operator. For example, apparatus 10 may include a plurality of status lights 64, one for each measured parameter. If a value falls outside its prescribed limits, the color of the status light may change. Or, an audio alarm may be sounded. Outputs from processor 54 are supplied to the quiet bus interface 52 through a dual port RAM 66. In addition to the status lights, the measured values may also be provided to a recording means such as a strip chart recorder 68 or similar device so a permanent record is obtained. The apparatus may further include an oscillograph 70 so a waveform can be displayed. For recording purposes, processor 54 is supplied an input (TACHO in FIG. 2) from drive unit 14 by which the location on the tube at which a particular measurement is taken can be noted.

As previously mentioned, tube T is rotated as it is drawn through chamber 12. Because of this, successive wall thickness measurements of the tube will be through different wall sections. By storing successive o.d., wall thickness, and i.d. values, computing means 60 can compute the ovality or eccentricity (ecc) of the tube. This information can also be compared with a set of limits and the results displayed or recorded in the manner previously described.

What has been described is a method and apparatus for the non-destructive testing of a tubing used in nuclear reactors or the like. The method and apparatus utilize ultrasonic waveforms to precisely measure the physical characteristics of the tubing. As described hereinabove, the method and apparatus are used to test lengths of tubing on a production basis and to provide quick and accurate readings of the physical properties of the tubing under test. The method and apparatus test to accuracies of 10 microinches using ultrasonic pulses whose times of flight are measured to an accuracy of 100 picoseconds. This is done at a rate of 10 khz. During testing in accordance with the method, the apparatus generates and transmits an ultrasonic waveform, and then receives and stores the return echo. The stored waveform is then subsequently processed to determine the physical characteristics of the tube under test, and whether the measured values fall within prescribed test limits. According to the method; the flight time of each pulse and its echo is mathematically reconstructed to determine the pertinent measurement information. The apparatus is calibrated prior to the beginning of each test cycle. Further, the apparatus independently monitors the testing environment during testing, and the test data is compensated for sensed environmental changes. This is done to maintain the accuracy of the test results. If an out-of-tolerance condition is sensed; an indication is printout of all the measured parameters so there is a permanent record of the measured properties for each tube tested. The apparatus is easy to use and provides the user with a wide variety of test options.

Finally, the method and apparatus of the invention provide a test technique applicable to a broad range of testing environments. By first storing each test waveform and its resulting echo, and then subsequently processing the results, true peak value and zero crossing points are readily determined. This allows accurate threshold comparisons and zero crossing references to be obtained and eliminates variations in the test results which occur in conventional testing methodologies.

In view of the foregoing, it will be seen that the several objects of the invention are achieved and other advantageous results are obtained.

As various changes could be made in the above constructions without departing from the scope of the invention, it is intended that all matter contained in the above description or shown in the accompanying drawings shall be interpreted as illustrative and not in a limiting sense.

Having thus described the invention, what is claimed and desired to be secured by Letters Patent is:

1. Apparatus for measuring the physical properties of an object using ultrasonics comprising:

means for generating an electrical pulse having a predetermined set of characteristics;

transmission means for converting said pulse to an ultrasonic waveform, simultaneously propagating the waveform at the object from at least two different directions, and for detecting respective reflected response waveforms from the object;

means for storing each response waveform and including a first converting means and a second converting means for respectively converting each response waveform from an analog signal to a digital signal, and memory means for storing the resultant digital contents of each converted waveform; and, processing means for simultaneously, separately reconstructing each response waveform and determining from each separate reconstruction a value representing a first physical characteristic of the object, said processing means including means for mathematically combining the respective values derived from the separate reconstructions to produce another value representating a second physical characteristic of the object, and said processing means further including means for comparing the values for each of the physical characteristics with a predetermined set of limits for each characteristic to determine if the characteristic values fall within said limits, a first processing channel for processing one of the converted waveforms, and a second and separate processing channel for processing the other converted waveform, each processing channel having as a data input the converted waveform digital contents stored in one of the respective converting means each channel including gate means for performing a real time comparison of the response waveform with predetermined threshold criteria for the response waveform to determine if the converted response waveform is to be processed by the processing means and a processor to which an output from the gate means is supplied, the output from the gate means providing the processor the location in the memory means of data to be used in reconstructing the converted waveform to measure times of flight, each said processor employing a linear interpolation technique and a finite impulse response technique on converted waveform data to reconstruct the waveform and determine accurate time of flight values, and said processing means further including a third processor to which the results of the operations of each channel processor are supplied, said results including each of the two respective characteristic values represented.

2. The apparatus of claim 1 wherein said transmission means includes a first ultrasonic transducer positioned adjacent said object at one location and a second ultrasonic transducer positioned adjacent said object at a second and separate location.

3. The apparatus of claim 2 wherein one said transducer is positioned 180° opposite said other transducer.

4. The apparatus of claim 2 wherein said generating means includes means for periodically supplying an electrical pulse to said transmission means, said transmission means supplying said pulse to each said transducer means simultaneously, and each said transducer means converting said electrical pulse to an ultrasonic waveform having said set of characteristics, propagating said waveform toward said object, receiving said reflected response waveform and converting said response waveform back into an electrical return pulse, and transmitting said return pulse to said storing means.

5. The apparatus of claim 4 further including means for compensating said response waveforms for changes in environmental conditions in a region in which the object and said first and second transducers are located.

6. The apparatus of claim 5 wherein said compensating means includes a third transducer exposed to the environment in said region and having a reference pulse output supplied as an input to said processing means together with the return pulse from each of the other said transducers, said processing means processing the reference output pulse together with the respective return pulses produced by said first and second transducers to adjust a value determined from said return pulses any environmental changes which may effect propagation times of an ultrasonic waveform produced by said transducers.

7. The apparatus of claim 1 wherein each said processing means channel includes bus means by which the processor for said channel can access the digital contents of its associated memory means to acquire said contents and determine a value of a physical property of the object represented thereby.

8. The apparatus of claim 1 wherein said third processor includes means for combining the values supplied by each of said channel processors to produce a third value representing a physical property of the object and for comparing the respective values with upper and lower value limits to determine if the respective values fall within the respective limits.

9. The apparatus of claim 8 further including output means for supplying an indication of the respective values and an indication of whether or not the values fall within their respective limits.

10. Apparatus for measuring the physical characteristics of a hollow tube comprising:

means for placing the tube in a liquid medium and for drawing the tube through the medium in a controlled manner;

means for periodically generating an electrical pulse having a predetermined set of characteristics;

transducer means for converting said pulse to an ultrasonic waveform; said transducer means including first and second ultrasonic transducers located in the liquid medium and spaced apart from each other and spaced from an outer sidewall surface of the tube a known distance, said ultrasonic transducers simultaneously propagating the waveform at the tube from two different directions and detecting a plurality of echoes from the tube, said ultrasonic transducers converting the echoes into electrical response waveforms;

receiver means for receiving and separately storing each resulting response waveform produced by said transducers; and, processing means for performing a real time comparison of the response waveform with predetermined threshold criteria for the response waveform to determine if the converted response waveform is to be processed by the processing means, and for simultaneously, separately reconstructing each response waveform and determining from each separate reconstruction values representing the thickness of the tube sidewall, said processing means including computing means for mathematically combining the respective tube thickness values derived from the separate reconstructions to determine the inner diameter of the tube, and said processing means further including means for comparing the respective tube sidewall thickness and computed tube inner diameter values with a predetermined set of limits for each of the values to determine if the values fall within said limits.

11. The apparatus of claim 10 wherein one said transducer is positioned 180° opposite said other transducer.

12. The apparatus of claim 10 wherein said pulse generating means generates pulses at a rate of approximately 10 KHz.

13. The apparatus of claim 10 wherein said receiving means includes a first converting means for converting one of the response waveforms, and a second converting means for converting the other response waveform, each converting means including means for convening the respective response waveforms from an analog signal to a digital signal and memory means for storing the digital contents of each converted waveform.

14. The apparatus of claim 13 wherein the processing means includes a first processing channel for processing one of the converted waveforms, and a second and separate processing channel for processing the other converted waveform, each processing channel having as a data input the converted waveform digital contents stored in one of the respective converting means.

15. The apparatus of claim 14 wherein each processing means channel includes gates means for performing the real time comparison of the response waveform with the predetermined threshold criteria, said threshold criteria including respective zero crossing times for each of a plurality of echoes included in said response waveform, and a processor to which an output from the gate means is supplied, said gate means output including locations in the memory means of data to be used in reconstructing the converted waveform to measure times of flight.

16. The apparatus of claim 15 wherein each said processor employs a linear interpolation technique and a finite impulse response technique on the converted waveform data to reconstruct the waveform and determine accurate time of flight values, and said processing means further includes a third processor to which the results of the operations of each channel processor are supplied, said results including the respective values represented.

17. The apparatus of claim 16 wherein said processing means includes a third processor to which results of the operations of each channel processor are supplied, said results including respective tube sidewall thickness values determined as a function of the time of flight information derived from each converted waveform, said third processor including means for subtracting the sidewall thickness values from a value established during a calibration of the apparatus and representing a distance between the respective transducers to compute the inner diameter of the tube, and means for comparing the respective values with upper and lower value limits to determine if the respective thickness values and computed inner diameter value fall within the respective limits.

18. The apparatus of claim 17 further including output means for supplying an indication of the respective values and an indication of whether or not the values fall within their respective limits.

19. The apparatus of claim 10 further including means for compensating the response waveforms for changes in environmental conditions within the liquid medium, said compensating means including a third transducer placed in the liquid medium and having an output supplied as a compensating input with the response waveform from each of the other two transducers, an electrical compensation response pulse produced by said third transducer being combined with the electrical return pulse produced by each of said other two transducers, said compensation response pulse being received and stored with each of the electrical response pulses from said other two transducers, and said processing means processing said compensation response pulse with each response pulse from said transducers to modify the values resulting from the processing of said return pulses for changes in the liquid medium.

20. A method of measuring the physical properties of an object using ultrasonics comprising:

generating an ultrasonic waveform having a predetermined set of waveform characteristics;

simultaneously propagating the waveform at the object from at least two different directions, and at a separate reference object;

detecting respective reflected response waveforms from the object and the reference object, each reflected response waveform representing an echo of the respective propagated waveform;

combining the reflected response waveform from the reference object with each reflected response waveform from the object and separately storing each combined reflected response waveform;

evaluating each combined reflected response waveform with a set of threshold criteria to determine if a combined reflected response waveform should be processed to derive values representing a first physical characteristic of the object;

simultaneously, separately reconstructing each combined reflected response waveform and determining from each separate reconstruction a value representing said physical characteristic of the object;

mathematically combining the respective values derived from the separate reconstructions to ascertain a second physical characteristic of the object; and, comparing each of the physical characteristic values with a predetermined set of limits for each of the values to determine if the measured values fall within said limits.

21. The method of claim 20 wherein generating said ultrasonic waveform includes periodically generating an electrical pulse having a predetermined set of characteristics, and converting said electrical pulse to said ultrasonic waveform.

22. The method of claim 21 wherein propagating said waveform at said object includes supplying said electrical pulse simultaneously to each of a first and a second ultrasonic transducer each of which converts said electrical pulse to an ultrasonic waveform and transmits the waveform at said object and to a third transducer which converts said electrical pulse to an ultrasonic waveform and transmits the waveform at said separate reference object.

23. The method of claim 20 wherein propagating said waveform further includes positioning said first and second transducers adjacent said object 180° apart from each other.

24. The method of claim 23 wherein detecting the respective reflected response waveforms from the object includes the ultrasonic transducers converting the reflected waveforms into electrical response waveforms, converting each electrical response waveform from an analog signal to a digital signal, and storing of the waveform includes storing the digital contents of each converted waveform in a memory means.

25. The method of claim 24 wherein reconstructing each reflected response waveform and determining from each separate reconstruction a value representing a physical characteristic of the object includes each processing in a separate processing channel the digital contents of each respective converted waveform.

26. The method of claim 25 wherein evaluating the reflected response waveform includes performing a real time comparison of the time of flight for portions of the reflected response waveform with predetermined threshold criteria representing desired times of flight for those portions, and, if the threshold values are met, supplying addresses in said memory means to a processing means to enable the processing means to process the digital response waveform data in those addresses to reconstruct the converted waveform.

27. The method of claim 26 wherein processing said digital data includes performing a linear interpolation and a finite impulse response on the converted waveform data to reconstruct the waveform and determine accurate time of flight values.

28. The method of claim 27 wherein mathematically combining the respective values derived from the separate reconstructions includes subtracting the values represented by each of the separate reconstructions from a predetermined value with the result representing yet another physical characteristic of the object.

29. A method for non-destructively measuring the physical characteristics of a hollow tube comprising:

placing the tube in a liquid medium and drawing the tube through the medium in a controlled manner;

periodically generating an electrical pulse having a predetermined set of characteristics;

converting said pulse to a first and a second ultrasonic waveform by simultaneously supplying said electrical pulse to a first and a second ultrasonic transducer located in the liquid medium, said transducers being spaced apart from each other and spaced a known distance from an outer sidewall surface of the tube, said ultrasonic transducers simultaneously propagating an ultrasonic waveform at the tube from two different directions;

further converting said pulse to a third ultrasonic waveform by simultaneously supplying said electrical pulse to a third ultrasonic transducer located in the liquid medium, said third transducer being spaced apart from a reference object, and said third transducer propagating an ultrasonic waveform at said reference object;

detecting echoes from the tube and the reference object and combining the echoes into separate combined, electrical response waveforms, one from each of said first and second transducer;

receiving and separately storing each resulting combined response waveform in a memory means;

reconstructing each response waveform and evaluating each reconstruction with a set of threshold criteria to determine if a response waveform should be processed to derive values representing the thickness of the tube; and simultaneously, separately processing each combined response waveform and determining from each separate reconstruction values representing the thickness of the tube sidewall, said processing including mathematically combining the respective tube thickness values derived from the separate reconstructions to determine an inner diameter of the tube, and comparing the respective tube sidewall thickness and computed tube inner diameter values with a predetermined set of limits for each of the values to determine if the values fall within said limits.

30. The method of claim 29 wherein propagating said waveform includes positioning said transducers adjacent said tube 180° apart from each other.

31. The method of claim 29 wherein receiving each propagated waveform and the resulting response waveform includes converting said resulting response waveform from an analog signal to a digital signal, and storing of the resulting digital contents of the converted waveform in said memory means.

32. The method of claim 31 wherein processing of the waveforms includes performing a real time comparison of the time of flight for portions of the response waveform with predetermined threshold criteria representing desired times of flight for those portions, and, if the threshold values are met, supplying addresses in said memory means to a processing means to enable the processing means to process the digital response waveform data in those addresses to reconstruct the converted waveform.

33. The method of claim 32 wherein processing the converted waveform digital data includes performing a linear interpolation and a finite impulse response on the converted waveform data to reconstruct the waveform and determine accurate time of flight values therefrom.

34. The method of claim 33 wherein mathematically combining the respective tube thickness values to determine the inner diameter of the tube includes subtracting each of the tube thickness values from a predetermined value representing the spatial separation between the ultrasonic transducers, with the remainder comprising the tube's inner diameter value.

35. The method of claim 34 further including recording the respective values to provide a permanent record thereof.

36. The method of claim 34 further including calibrating the ultrasonic transducers prior to testing a tube to establish a known distance between the respective transducers.

37. The method of claim 29 further including providing an indication if any of the values fall outside the limits.

* * * * *